US009999357B2

(12) United States Patent
Sola i Caros et al.

(10) Patent No.: US 9,999,357 B2
(45) Date of Patent: Jun. 19, 2018

(54) METHOD AND APPARATUS FOR THE NON-INVASIVE MEASUREMENT OF PULSE TRANSIT TIMES (PTT)

(71) Applicant: CSEM CENTRE SUISSE D'ELECTRONIQUE ET DE MICROTECHNIQUE SA-RECHERCHE ET DÉVELOPPEMENT, Neuchâtel (CH)

(72) Inventors: Josep Sola i Caros, Neuchâtel (CH); Josef X. Brunner, Chur (CH); Damien Farrario, Vevey (CH); Andrew Adler, Ottawa (CA)

(73) Assignee: CSEM CENTRE SUISSE D'ELECTRONIQUE ET DE MICROTECHNIQUE SA-RECHERCHE AT DÉVELOPPEMENT, Neuchatel (CH)

( * ) Notice: Subject to any disclaimer, the term of this patent is extended or adjusted under 35 U.S.C. 154(b) by 577 days.

(21) Appl. No.: 13/739,025

(22) Filed: Jan. 11, 2013

(65) Prior Publication Data

US 2013/0123617 A1    May 16, 2013

Related U.S. Application Data

(63) Continuation of application No. PCT/EP2011/061753, filed on Jul. 11, 2011.
(Continued)

(51) Int. Cl.
*A61B 5/05* (2006.01)
*A61B 5/021* (2006.01)
(Continued)

(52) U.S. Cl.
CPC ........ *A61B 5/02125* (2013.01); *A61B 5/0035* (2013.01); *A61B 5/02233* (2013.01);
(Continued)

(58) Field of Classification Search
None
See application file for complete search history.

(56) References Cited

U.S. PATENT DOCUMENTS 4,425,902 A * 1/1984 Thouault ................. F23C 3/004
                                                    122/33
6,228,033 B1 * 5/2001 Koobi ................ A61B 5/02007
                                                    600/483
(Continued)

FOREIGN PATENT DOCUMENTS

WO      2008004159 A2     1/2008
WO   WO 2008149125 A1 * 12/2008 ............. A61B 5/053

OTHER PUBLICATIONS

Bang et al., "A Pulse Transit Time Measurement Method Based on Electrocardiography and Bioimpedance," IEEE, 2009, pp. 153-156.*
(Continued)

*Primary Examiner* — James Kish
(74) *Attorney, Agent, or Firm* — Pearne & Gordon LLP

(57) ABSTRACT

A method and apparatus for measuring a pulse transit time (PTT) value of a subject, comprise measuring a first arterial pressure pulse arrival time (PAT) and measuring a second PAT value; calculating a PTT value from the difference between the first PAT value and the second PAT value; processing a sequence of electrical impedance tomography (EIT) images to identify at least one region of interest (ROI); and estimating at least one of the first and second PAT value from the variation of impedance value determined from the at least one ROI. The method allows for the non-invasive
(Continued)

and continuous measurement of the PTT value and arterial blood pressures.

16 Claims, 10 Drawing Sheets

Related U.S. Application Data

(60) Provisional application No. 61/344,409, filed on Jul. 16, 2010.

(51) Int. Cl.
*A61B 5/024* (2006.01)
*A61B 5/053* (2006.01)
*A61B 5/00* (2006.01)
*A61B 5/022* (2006.01)
*A61B 5/029* (2006.01)

(52) U.S. Cl.
CPC ...... *A61B 5/02438* (2013.01); *A61B 5/02444* (2013.01); *A61B 5/0536* (2013.01); *A61B 5/029* (2013.01)

(56) References Cited

U.S. PATENT DOCUMENTS

| | | | | |
|---|---|---|---|---|
| 6,236,886 | B1* | 5/2001 | Cherepenin | A61B 5/0536 600/547 |
| 6,648,828 | B2* | 11/2003 | Friedman | A61B 5/021 600/485 |
| 2003/0105410 | A1* | 6/2003 | Pearlman | 600/547 |
| 2003/0216664 | A1* | 11/2003 | Suarez | 600/547 |
| 2006/0247538 | A1* | 11/2006 | Davis | 600/481 |
| 2008/0146925 | A1* | 6/2008 | Byrd et al. | 600/438 |
| 2008/0319356 | A1* | 12/2008 | Cain et al. | 601/2 |
| 2009/0163821 | A1 | 6/2009 | Sola i Caros | |
| 2010/0215225 | A1* | 8/2010 | Kadomura et al. | 382/128 |
| 2010/0228136 | A1* | 9/2010 | Keel | A61B 5/02416 600/507 |
| 2010/0268109 | A1* | 10/2010 | Wang | 600/547 |

OTHER PUBLICATIONS

Halter et al., "Video rate electrical impedance tomography of vascular changes: preclinical development." Physiol. Meas. 29 (2008) 349-364.*

Rasicher et al., "Impedance plethysmography for the evaluation of pulse-wave velocity in limbs." Med. & Biol. Eng. & Comput. 1993, 31, pp. 318-322.*

Sola et al., "Parametric estimation of pulse arrival time: a robust approach to pulse wave velocity." Physiol. Meas. 30 (2009) 603-615.*

"Ambulatory monitoring of the cardiovascular system: the role of Pulse Wave Velocity", J. Solà et al., Chapter in New Developments in Biomedical Engineering, ISBN 978-953-7619-57-1, Austria, 2010.

Chen W. et al, "Continuous estimation of systolic blood pressure using the pulse arrival time and intermittent calibration", Medical & Biological Engineering & Computing 2000, vol. 38.

"Localisation of cardiac related impedance changes in the thorax", B. N. Eyüboglu et al., Clin. Phys. Phyiol. Meas. 1987, vol. 8.

"Pulmonary perfusion and ventricular ejection imaging by frequency domain filtering of EIT images", M. Zadehkoochak et al., Clin. Phys. Physiol. Meas., 1992, vol. 13.

"Noninvasive Assessment of Right Ventriclar Diastolic Function by Electrical Impedance Tomography", A. V. Noordegraaf, et al., Chest, 1997, vol. 111.

"Determination of stroke volume by means of electrical impedance tomography", A. V. Noordegraaf, et al., Physiol. Meas., 2000, vol. 21.

"Dynamic separation of pulmonary and cardiac changes in electrical impedance tomography", J. M. Deibele, et al., Physiol. Meas., 2008, vol. 29.

"Separation of ventilation and perfusion related signals within EIT-data streams", R. Pikkemaat, et al., Proc. Int. Conf. Electrical Bioimpedance, Journal of Physics: Conference Series 224, 2010.

"Parametric estimation of pulse arrival time: a robust approach to pulse wave velocity", J. Solà, et al., Physiol. Meas., 2009, vol. 30.

International Search Report for PCT/EP2011/061753 dated Dec. 28, 2011.

* cited by examiner

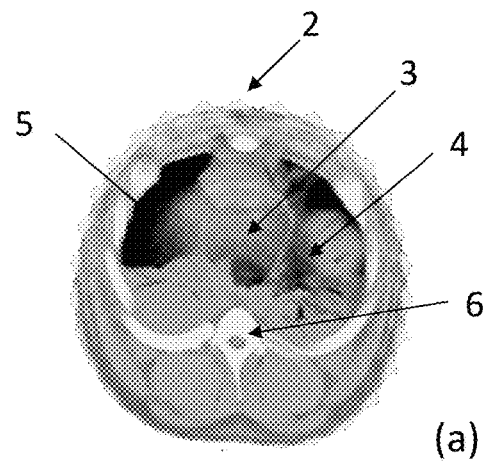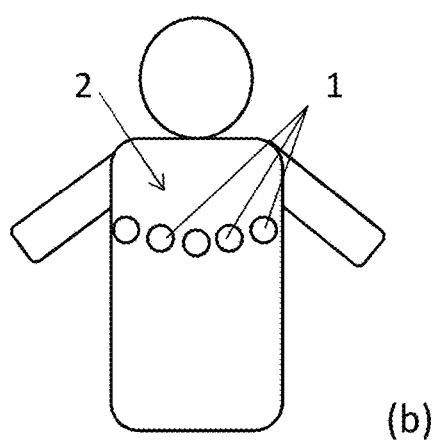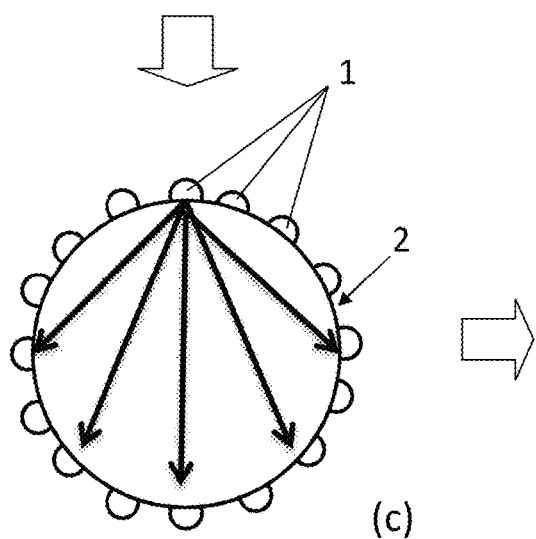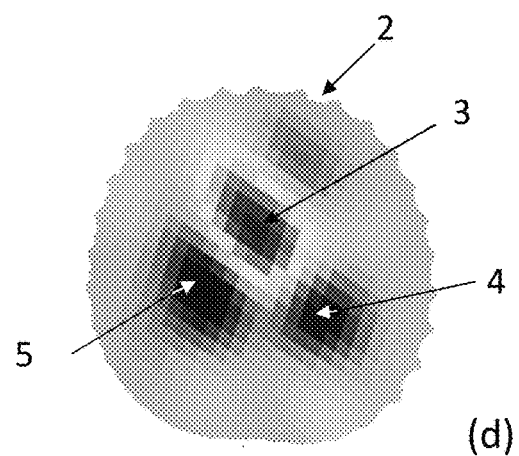
Fig. 1 (State of art)

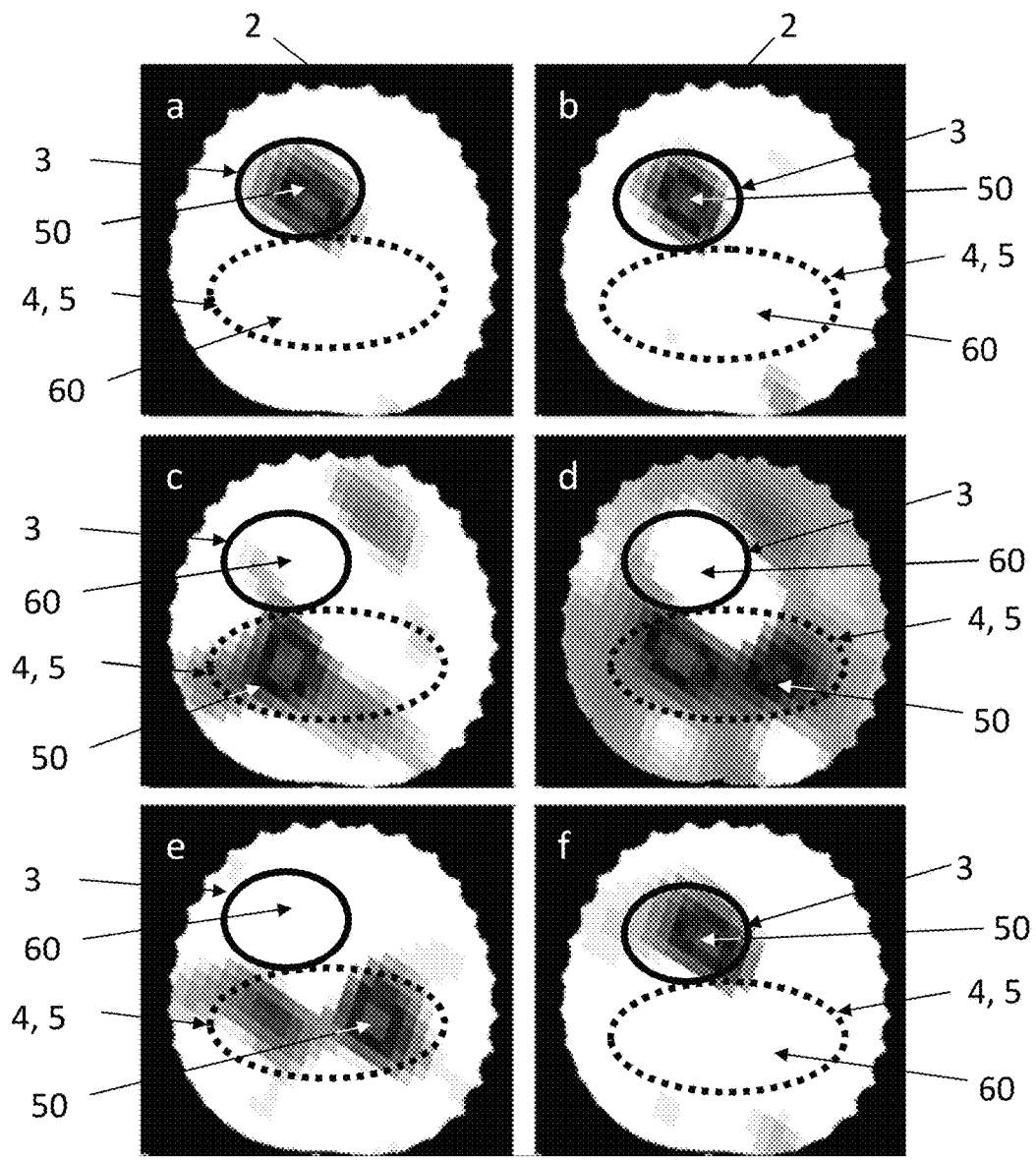
Fig. 2 (State of art)

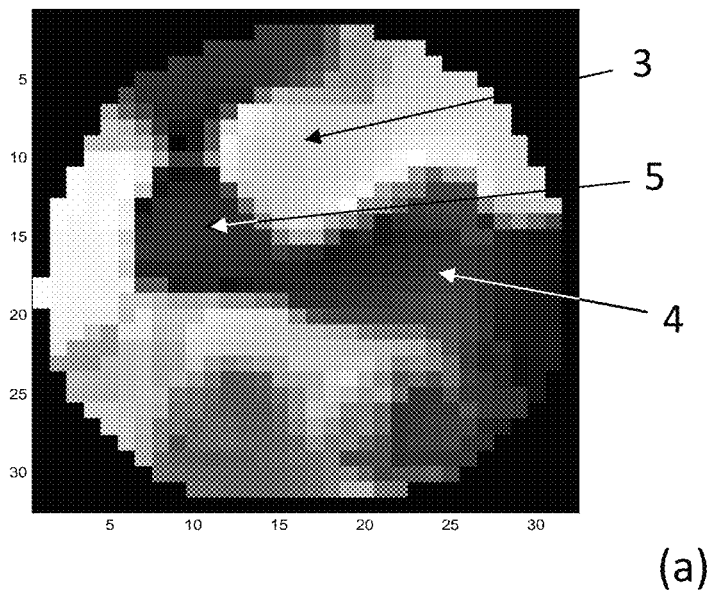
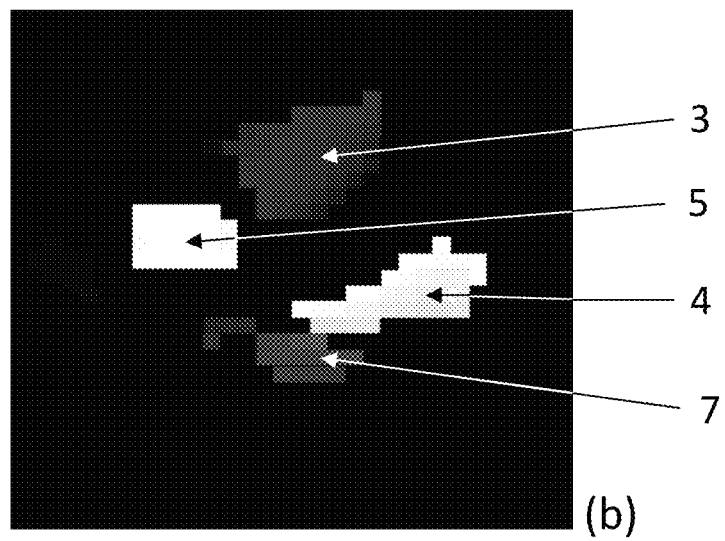
Fig. 3 (State of art)

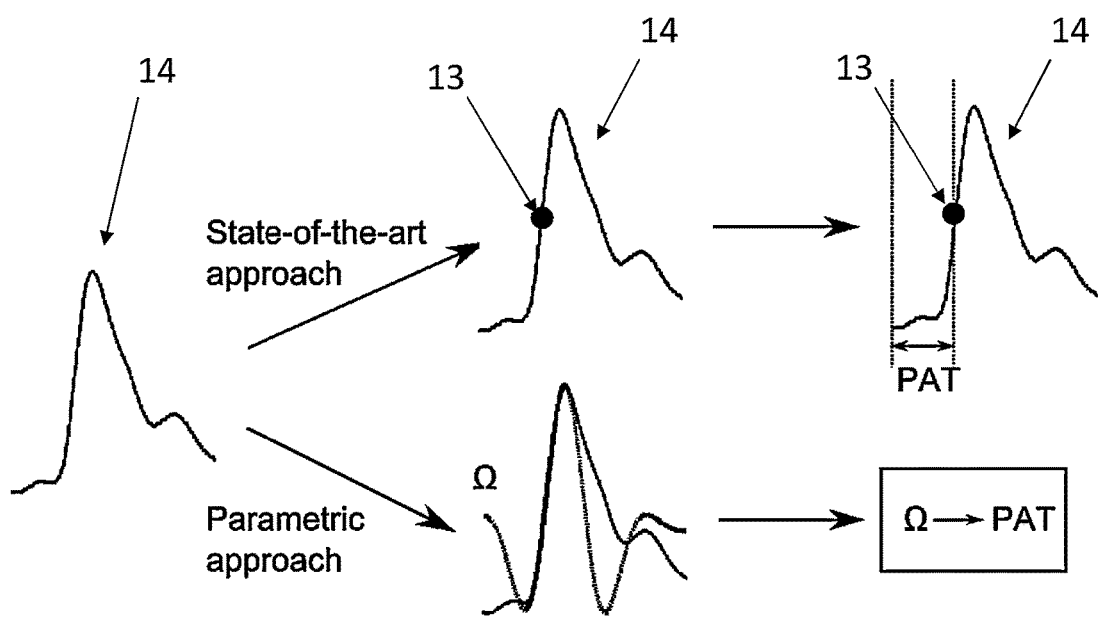
Fig. 4 (State of art)

METHOD AND APPARATUS FOR THE NON-INVASIVE MEASUREMENT OF PULSE TRANSIT TIMES (PTT)

FIELD

The present disclosure relates to a method and apparatus for the non-invasive and continuous monitoring of pulse transit time (PTT) value of a subject. The invention relates as well to the non-invasive and continuous measurement of arterial blood pressures.

DESCRIPTION OF RELATED ART

The demand for devices to assess and monitor human cardiovascular function continuously and in real time in a non-invasive and non-obtrusive way in both, clinical and ambulatory conditions is steadily increasing: while reducing the need for long hospitalization periods, non-invasive monitors also reduce healthcare costs, improve patient comfort and safety. In recent years, electrocardiograms, intermittent blood pressure monitors and pulse oximeters have been successfully released into the market paving the way towards the monitoring of cardiac and vascular parameters in hospitals and in out-patients alike. Unfortunately, these parameters still provide an incomplete picture of a patient's health status and do not fully meet clinical demand. As an example, discontinuous intermittent measurements of blood pressure during daytime are unsuitable to pick up clinically significant changes in blood pressure during sleep, especially during sleep apnea, one of the known causes of hypertension.

Non-Invasive Measurement of Pulse Wave Velocity—

Pulse wave velocity (PWV) represents the velocity at which pressure pulses propagate through the arterial tree of a subject (animal or human). PWV is considered the gold standard methodology to assess arterial wall stiffness, and has been identified as an independent predictor of cardiovascular morbidity and mortality. In line with this data, in 2007 the European Society of Hypertension has introduced PWV as a recommended test to assess cardiovascular risk in its guidelines for the diagnosis and management of hypertension. Nowadays techniques that allow assessment of PWV non-invasively fall into two main categories.

On the one hand, COMPLIOR® (Colson, France), SphygmoCor® (AtCor Medical, Australia), Vicorder® (Skidmore Medical, UK) and PulsePen® (Diatecne, Italy) rely on the placement of two pressure transducers onto two superficial arteries at distinctly different distances from the heart. These devices detect the arrival time of a pressure pulse that propagates through the arterial tree, and calculate the delay in pulse arrival times between the proximal and distal sensors. By approximating the distance through which the pulse has propagated, one estimates then a pulse propagation velocity value. Large clinical studies support the reliability and clinical validity of this technique. These devices require the presence of trained medical staff to be operated.

On the other hand, Arteriograph® (TensioMed, Hungary) estimates aortic PWV by applying pulse wave analysis techniques to a pressure pulse recorded by an inflated brachial cuff. The major advantage of this approach is that PWV measurements can be performed automatically, reducing the need for trained medical staff. The measurement is based on the fact that during systole, the blood volume having been ejected into the aorta generates a pressure pulse (early systolic peak). This pulse travels down the aorta and reflects from its bifurcation, creating a second pulse (late systolic peak). The return time (RT S35) is the time difference between the arrival of the first and the second systolic pulse waves, and is claimed to be a surrogate of aortic PWV. Unfortunately, clinical and numerical studies currently question the reliability and working principles of the RT S35 technique.

A broader review on the technical and physiological background of the described techniques is provided in Reference 1: "Ambulatory monitoring of the cardiovascular system: the role of Pulse Wave Velocity", J. Solà et al., Chapter in New Developments in Biomedical Engineering, ISBN 978-953-7619-57-1, Austria, 2010.

A first approximation of the continuous non-invasive measurement of central or aortic PWV is described in unpublished provisional patent application U.S. 61/318,444, filed on Mar. 29, 2010, also describing a device that estimates PWV values from the aortic valve to the vasculature supplying the anterior thoracic skin in the sternal region. It is well known that reliable PWV measurements for the estimation of systemic arterial blood pressure have to be conducted in non-muscular central elastic arteries such as the aorta. Any involvement of arteries that are subjected to vasomotion (i.e. vasoconstriction) will influence the pressure estimates in an unpredictable way. Due to the biomechanics of the particular segments of the arterial tree involved in the pulse propagation, with the main passage of the pressure pulse (85% of the distance) occurring within arteries of the elastic type (i.e. the aorta) before branching into arteries of the muscular type for the short remaining distance (i.e. the mammary artery) to the chest sensor, the PWV values measured by the technique disclosed in U.S. 61/318,444 are good approximations of truly aortic PWV values. The described method and apparatus have the advantage of being operated in a fully unsupervised manner, facilitating thus the measurement of PWV in ambulatory scenarios.

However, the state of the art does not disclose a method which is based on a continuous and non-invasive measurement of Pulse Wave Velocity directly within the elastic aorta as such.

Use of Electrical Impedance Tomography (EIT) to Assess Cardiovascular Parameters—

From an electrical perspective, the thoracic cavity can be viewed as a complex distribution of impedance volumes. While the lungs (filled with air cavities) form high impedance volumes, the heart (filled with blood) forms a compact impedance volume and branching blood vessels low impedance volumes. Reference 2: "Electrical Impedance Tomography:Methods, History and Applications", David S. Holder. Institute of Physics, Series on Medical Physics and Biomedical Engineering, ISBN 0 7503 0952 0, 2005, describes tomographic reconstructions of the distribution of impedances within the thoracic cavity, created by electrical impedance tomography (EIT).

As input signals, EIT requires a set of impedance measurements performed around the chest 2 (see FIG. 1 (b)). Basic a-priori knowledge about chest anatomy allows then to estimate the most likely impedance distribution given the set of measurements, and to determine specific regions of interest, such as the heart and the lungs. With the help of EIT technology, fast in-vivo functional images (versus morphological, anatomical or structural images) of the thoracic cavity (up to 50 images/second) can be obtained simply requiring the placement of several electrodes around the thorax (e.g., in a simple chest belt or in more sophisticated anatomy-adjusted configurations). FIGS. 1(a) to (d) represent an example of estimation of blood movement within the chest using EIT. More particularly, FIG. 1(b) shows after placing several electrodes 1 around the chest 2; FIG. 1(c) shows impedance measurements being performed for each electrode pair 1, where the arrows represent different electrical propagation paths; and FIG. 1(d) shows tomographic images being constructed with the dark areas representing the heart 3, the right lung 4 and left lung 5. By analyzing a series of images obtained during a complete cardiac cycle, one obtains information on the cyclic movement of blood within the chest 2. A computed tomography (CT) scan of pig chest is provided as anatomical reference (see FIG. 1(a)). In the CT-scan of FIG. 1(a) the heart 3, right lung 4, left lung 5, and back bone 6 are visible.

During each cardiac cycle vascularized structures within the thorax receive bursts of highly electrically conductive blood which decreases their local impedance provided these vessels expand locally. Furthermore, the transitions in the flow characteristics of the intra-aortic blood from a turbulent towards a more laminar flow during a heartbeat also cause the electrical characteristics of the blood to change in a cyclic way. Hence, when looking at a sequence of EIT images acquired during a complete cardiac cycle, one is able to visualize pulsations of the impedance signal (impedance pulse) that are associated to underlying blood pulsation phenomena (pressure pulse) occurring at some pulsating structures. These pulsating structures are either the heart as such or major vessels running either within the EIT field of observation (pulmonary artery) or through it (aorta). An example of EIT-based visualization of blood pulsation from the heart to the lungs of an anesthetized pig is illustrated in FIGS. 2(a) to (f). More particularly, FIGS. 2(a) to (f) illustrate the tracking of blood as it moves through the heart 3 and lungs 4, 5 during a cardiac cycle. EIT images show the local filling of blood in the areas indicated by the numeral 50 and emptying in the areas indicated by the numeral 60. The heart region 3 has been delineated in solid black line and the lung regions 4, 5 in dashed black lines. In FIGS. 2(a) and (b) one observes the filling of the heart 3. In FIG. 2(c) the heart 3 empties while the right lung 4 (here on the left hand side) is starting to be perfused. In FIGS. 2(d) and (e) both lungs 4, 5 are perfused. Finally, in FIG. 2(f) the cardiac cycle starts again.

In the following, the state of the art on the assessment of cardiovascular parameters by means of the analysis of sequences of EIT images is described.

Reference 3: "Localisation of cardiac related impedance changes in the thorax", B. N. Eyüboglu et al., Clin. Phys. Phyiol. Meas. 1987, Vol 8, first proposed to analyze the changes in impedance distribution within the thorax during a full cardiac cycle. By comparing the changes in impedance distribution across the different EIT images, they described the filling and emptying of the ventricles and the perfusion of the lungs.

Reference 4: "Pulmonary perfusion and ventricular ejection imaging by frequency domain filtering of EIT images", M. Zadehkoochak et al., Clin. Phys. Physiol. Meas., 1992, Vol 13, proposed a method to decompose a sequence of EIT images into its pulmonary (ventilation) and its cardiogenic (perfusion) components, based on a frequency-domain analysis. Reference 5: "Noninvasive Assessment of Right Ventriclar Diastolic Function by Electrical Impedance Tomography", A. V. Noordegraaf, et al., Chest, 1997, Vol 111, proposed a method to assess ventricular diastolic function by, first, identifying the heart region within a sequence of EIT images, and by monitoring the changes of impedance at the identified region occurring during the different phases of the cardiac cycle. Identification of the heart chambers was performed by visualizing the changes of impedance distribution in an ECG-gated EIT image sequence.

Reference 6: "Determination of stroke volume by means of electrical impedance tomography", A. V. Noordegraaf, et al., Physiol. Meas., 2000, Vol 21, describes measuring Stroke Volume changes via a similar method as in Reference 5. Here, however, the identification of the heart region was done by averaging EIT pixel data through a full cardiac cycle. By setting a threshold on the amount of impedance change, those pixels exceeding the threshold were assigned to the heart region of interest (ROI). An energy feature for each pixel was thus defined.

Reference 7: "Dynamic separation of pulmonary and cardiac changes in electrical impedance tomography", J. M. Deibele, et al., Physiol. Meas., 2008, Vol. 29, also discloses a method to decompose a sequence of EIT images into its pulmonary (ventilation) and its cardiogenic (perfusion) component, based on a Principal Component Anaylsis.

Reference 8: "Separation of ventilation and perfusion related signals within EIT-data streams", R. Pikkemaat, et al., Proc. Int. Conf. Electrical Bioimpedance, Journal of Physics: Conference Series 224, 2010, proposes and analyses different methods to separate ventilation-related from perfusion-related regions within sequences of EIT images by analyzing the energy that pixels depict within different frequency bands.

In 2010 Sola et al. filed a U.S. provisional patent application Ser. No. 61/344,399 on a novel method for analyzing sequences of EIT images and for identifying organs and anatomical structures of interest based on the estimation of the arrival times of pressure pulses at the different anatomical locations within the EIT field of observation. By associating to each pixel a Pulse Arrival Time (PAT) value, a time-based image is generated. FIGS. 3(a) and (b) illustrate an example of PAT-based image constructed from a sequence of EIT images recorded in an anesthetized pig, according to U.S. provisional patent application Ser. No. 61/344,399. More particularly, bright colors (visible as white in FIG. 3) depict early arrival of pressure pulses while dark colors (visible as black in FIG. 3) depict later arrival of pressure pulse. FIG. 3(a) illustrates PAT values calculated for all pixels in the EIT image, including those pixels for which PAT estimation was not reliable. FIG. 3(b) illustrates PAT values calculated only for those pixels for which PAT estimation was reliable according to predefined criteria.

Moreover, U.S. provisional patent application Ser. No. 61/344,399 describes the relationship between physiologically meaningful pressure pulses within the thorax and impedance changes observed in a sequence of EIT images (the so-called impedance pulses). In particular it is stated that each time a pressure pulse reaches a segment of the arterial tree (either at the systemic or pulmonary circulation), it induces a temporary increase of the volume of conductive blood, locally decreasing the electrical impedance, and generating thus a so-called impedance pulse. Hence, an impedance pulse as measured by EIT is a surrogate of the underlying physiological phenomenon: a pressure pulse. Accordingly, it is concluded that although the amplitude information contained within impedance pulses (in Ohms) is difficult to associate with the amplitude information of pressure pulses (in mmHg), the timing information coded within the impedance pulse waveforms and within the pressure pulse waveforms is equivalent. In particular, the onset of a pressure pulse at a given anatomical location instantaneously induces the onset of the associated impedance pulse. Hence, Pulse Arrival Time (PAT) values extracted from impedance pulses correspond to PAT values extracted from pressure pulses, in terms of seconds. Hence, although PAT values illustrated by FIGS. 3(a) and (b) were estimated by analyzing impedance pulses within a sequence of EIT images, they correspond to PAT values of the pressure pulses arriving at the different anatomical regions.

A method for the robust detection of the arrival times of pressure pulses at different segments of the arterial tree has already been described in Reference 9: "Parametric estimation of pulse arrival time: a robust approach to pulse wave velocity", J. Solà, et al., Physiol. Meas., 2009, Vol. 30. Accordingly, the parametric modeling of pressure pulse waveforms provide a single pulse arrival time value (PAT) for each pressure tracing. While direct pressure tracings are obtained by means of an arterial line, examples of surrogate measurements are: photo-plethysmographic recordings, ultra-sound recordings and pixel-based MRI recordings. An example of a parametric estimation of PAT is provided in FIG. 4. In FIG. 4, conventional estimation PAT consists of detecting a characteristic point 13 within the pressure pulse waveform 14. Parametric estimation of PAT consists of first fitting a parametric model to the original pressure pulse waveform 14, and then processing the parameters of the model in order to obtain PAT equivalent values.

State of the art cited above does not disclose processing a sequence of EIT images for detecting in an automatic and unsupervised manner those pixels containing pulsatile information of the descending aorta for estimating aortic PWV and/or arterial blood pressure. Using aortic PWV and/or arterial blood pressure for the assessment of the pulmonary circulation is also not mentioned.

Continuous, Non-Invasive and Non-Obtrusive Measurement of Blood Pressure—

For assessing the vascular status or the blood pressure of the subject one is interested in estimating PTT values from pressure pulses that are propagating through elastic arteries of the patient, such as the aorta. Unfortunately, assessing pressure pulses within these proximal arterial regions requires the uses of invasive sensors such as arterial catheters.

Several methods for processing PTT or PWV values in order to provide continuous, non-invasive and non-obtrusive blood pressure (BP) measurements are described in the state of the art. For example, Reference 10: Chen W. et al, "Continuous estimation of systolic blood pressure using the pulse arrival time and intermittent calibration", Medical & Biological Engineering & Computing 2000, Vol. 38, discloses a method for deriving BP values from PWV values comprising the measurement of a reference BP value using a brachial cuff, where the brachial cuff can be automatically and intermittently inflated. In this method, PWV values are calibrated using the measured reference BP values together with the calibrated PWV values and intermittently measured BP values are interpolates on a beat by beat basis.

Calibration strategies for calculating PWV-derived values of BP are reviewed in Reference 1. In particular, patent application US20090163821 describes a method for improving the accuracy of PWV-derived BP calculations by introducing a cardiac output measurement. While BP measurements are performed by an oscillometric brachial cuff, cardiac output measurements can be performed by bio-impedance techniques, or by peripheral pressure pulse contour analysis techniques.

Methods disclosed in the state of the art concern calculating BP values from PWV values measured at distal (and thus muscular) segments of the arterial tree. Since muscular arteries exert vasomotion, i.e. changes in diameter and stiffness of the artery as driven by the central nervous system, the known methods require frequent calibrations procedures to compensate for such changes. Changes in orthostatic pressure induced by changes in body position also affect the known methods.

SUMMARY

The present disclosure concerns a method for measuring a pulse transit time (PTT) value of a subject, comprising: estimating a first pulse arrival time (PAT); estimating a second PAT value; and calculating a pulse PTT value from the difference between the first and second PAT values; wherein, the method further comprises: providing an electrical impedance tomography (EIT) imaging device adapted to record impedance signal distribution (EIT image) of the subject; during a predetermined measuring time period, measuring a sequence of temporally discrete EIT images of the subject using the EIT imaging device, each EIT image comprising a plurality of pixels, each pixel representing an impedance value; and determining at least one region of interest (ROI) comprising a subset of said plurality of EIT pixels. Said at least one PAT value is estimated from the variation of impedance value determined from the subset of said at least one ROI during the predetermined measuring time period.

In an embodiment, the method can comprise the steps of: a) processing a sequence of EIT images to identify at least two Regions Of Interest (ROI), b) measuring at least one arrival time of at least one impedance pulse for each identified ROI, and c) calculating a PTT value as the difference between the at least two arrival time values.

In another embodiment, at least one Region of Interest (ROI) can be defined by the analysis of impedance pulses; or manually by a human observer; or by manual or automatic analysis of a computer tomogram, an x-ray image, or another imaging method; or by manual or automatic analysis of a an image created by electrical impedance tomography; or a combination of any of the above methods.

In yet another embodiment, one ROI relates to the left ventricle and a second ROI relates to the descending aorta.

In yet another embodiment, the left ventricle can be identified as the ROI whose pixels depict the lowest PAT values in the time-based EIT image, and the aorta is identified as the ROI whose pixels depict the lowest PAT values in the dorsal thorax behind the lung ROIs.

In yet another embodiment, one ROI relates to the right ventricle and a second ROI relates to the pulmonary artery.

In yet another embodiment, the right ventricle can be identified as the ROI whose pixels depict the lowest PAT values in the time-based EIT image, and the pulmonary artery is identified as the ROI within the central lung region whose pixels depict the PAT values higher than those of the aorta but lower than those depicting the peripheral lung tissue.

In yet another embodiment, the method can further comprise, measuring at least two PTT values, assigning a blood pressure (BP) value to each measured PTT value, calculating a calibration factor for the conversion of PTT to BP, and calibrating subsequent measurements of PTT values with said calibration factor to obtain BP values. Reference BP values can be obtained using a brachial cuff or an arterial line.

In an alternative embodiment, the method comprises the steps of: a) processing a sequence of EIT images to identify at least one Regions Of Interest (ROI); b) measuring at least one arrival time of at least one impedance pulse for each identified ROI; c) calculating a PTT value as the difference between the measured arrival time value and an external time value.

In yet another embodiment, the external time value can be the R-Wave in an Electro-Cardiogram, or can correspond to the opening of the aortic valve as determined by a phonocardiogram, or can be the opening of the aortic valve as determined by an impedance cardiogram.

In yet another embodiment, the measured PTT values is transformed into a Pulse Wave Velocity (PWV) value comprising the steps of: a) measuring the arterial path length (APL) through which the pressure pulse has travelled, and b) calculating PWV=APL/PTT. The APL value can be obtained by manual or automatic analysis of a computer tomogram, an x-ray image, or another imaging method, or by measuring at least one morphological measurement of the patient, or a combination of any of the above methods.

The present disclosure also pertains to an apparatus for performing the method disclosed, and comprising: the electrical impedance tomography (EIT) imaging device comprising electrodes (1) for recording impedance signal distribution (EIT image) of the subject, and measuring the sequence of temporally discrete EIT images; a processing unit (22) adapted for performing the step of said estimating a first and second PAT value, estimating at least one ROI, and calculating the PTT value; and an output module for outputting the PTT value.

The method overcomes the known drawbacks of the state the art and is capable of measuring PTT values within central elastic arteries such as the aorta or the pulmonary artery in a fully non-invasive, continuous, automatic and unsupervised way. The present device and method overcome the drawbacks by measuring PTT values using impedance pulses measured by non-invasive tomographic techniques such as electrical impedance tomography (EIT). Since the timing information provided by impedance pulses is the same as the timing information provided by pressure pulses within the structure of interest, the main advantage of this new approach are its non-invasiveness and ease of use.

BRIEF DESCRIPTION OF THE DRAWINGS

The invention will be better understood with the aid of the description of an embodiment given by way of example and illustrated by the figures, in which:

FIGS. 1(a) to (d) represent an estimation of blood movement within the chest using Electrical Impedance Tomography (EIT);

FIGS. 2(a) to (f) show tracking of blood as it moves through the heart and lungs of an anesthetized pig during a cardiac cycle;

FIG. 3 illustrates (a) PAT values calculated for all pixels in an EIT image, and (b) PAT values calculated for those pixels for which PAT estimation was reliable;

FIG. 4 illustrates an exemplary parametric estimation of pulse arrival time;

DETAILED DESCRIPTION OF POSSIBLE EMBODIMENTS

Figure 5:
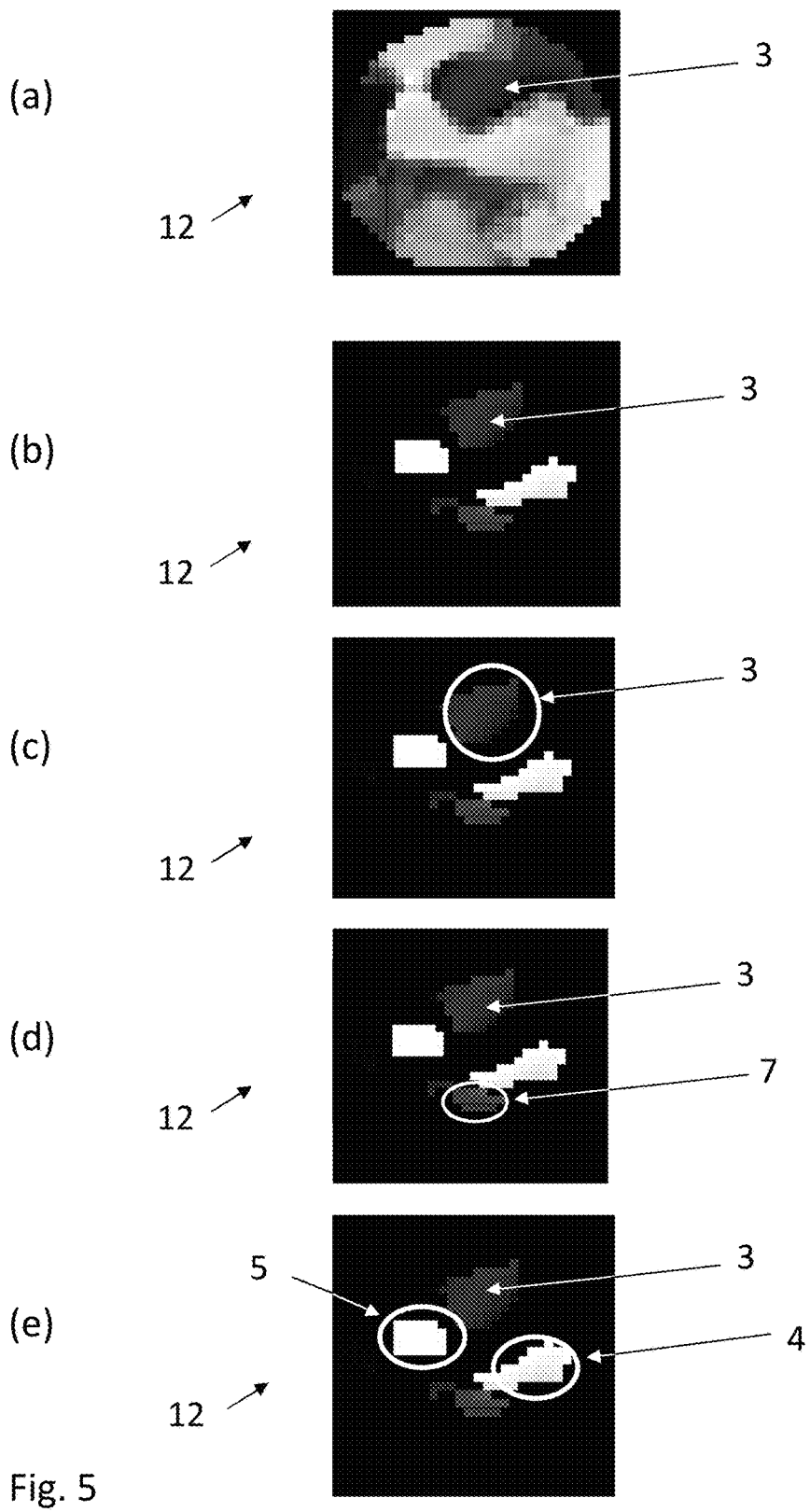
FIGS. 5(a) to (e) illustrate the detection of regions of interest (ROI) using time-based EIT imaging, according to an embodiment.

For assessing the vascular status or the blood pressure of a patient one is interested in estimating pulse transit time (PTT) values from pressure pulses that are propagating through elastic arteries of a subject (human or animal), such as the aorta. Unfortunately, assessing pressure pulses within these proximal arterial regions requires the uses of invasive sensors such as arterial catheters. The present disclosure concerns the measurement of a pulse arrival time (PAT) value in a proximal location of the arterial tree, and the measurement of a PAT value in a corresponding distal location of the arterial tree. A PTT value is finally calculated as the difference between both PAT values.

In an embodiment, a method for determining a pulse transit times (PTT) value from pressure pulses propagating in the arterial tree of a subject (human or animal) comprises:

measuring a first arterial pressure pulse arrival time (PAT), and measuring a second arterial pressure pulse arrival time (PAT) value; and calculating the PTT value from the difference between the first PAT value and the second PAT value;

processing a sequence of electrical impedance tomography (EIT) images to identify at least one region of interest (ROI); and estimating at least one of the first and second PAT value from the variation of an impedance value determined from said at least one ROI.

Said processing a sequence of EIT images can comprise providing an electrical impedance tomography (EIT) imaging device adapted to record impedance signal distribution (EIT image) of the subject; and during a predetermined measuring time period, measuring a sequence of temporally discrete EIT images of the subject using the EIT imaging device, each EIT image comprising a plurality of pixels, each pixel representing an impedance value. Said at least one ROI can comprise a subset of said plurality of EIT pixels; and said at least one PAT value is estimated from the variation of impedance value determined from the subset of said at least one the first ROI during the predetermined measuring time period.

In an embodiment, the at least one of the first and second PAT value is estimated by generating a time series corresponding to the variation of the impedance value during the predetermined measuring time period.

In an embodiment, said at least one ROI comprises a first ROI at a first, or distal, location of the arterial tree of the subject, and a second ROI at a second, or proximal, location of the arterial tree of the subject. In particular, for assessing the systemic circulation the left ventricle is proposed as a preferred proximal location for such a first measurement site while the descending aorta is proposed as a preferred distal location. According to the preferred locations, the calculated PTT provides information on the time it takes for the pulse to travel from the second to the first location, thus the pulse passing the aortic arch. On its way the pressure pulse travels through a purely elastic segment of the arterial tree. In the above example, the first location, or distal location, corresponds to the region of the descending aorta, and the second location, or proximal location, corresponds to the region of the left ventricle.

The same method can also be applied to the pulmonary circulation with the right ventricle being the preferred second (proximal) and a major branch of the pulmonary artery being the preferred first (distal) site of measurement. In the above example, the first location, or distal location, corresponds to the region of the major branch of the pulmonary artery, and the second location, or proximal location, corresponds to the region of the right ventricle.

The method can further comprise automatically detecting those pixels within a sequence of EIT images corresponding to the left ventricle on the one hand and the descending aorta on the other. In particular the invention describes an identification method based exclusively on the analysis of time-based EIT images. Initially, a time-based image is generated according to the state of the art US provisional patent application Ser. No. 61/344,399, where a PAT value is computed for each pixel in the sequence of EIT images.

In the case the second (or proximal) ROI is located in the region of the left and/or right ventricle, since the contraction of the heart is the first event of every cardiac cycle, a ROI corresponding to the heart (heart ROI) can be identified as those pixels being situated in front of the lungs (anterior location) that depict the earliest onset of the impedance pulse (small PAT values on the time-based image). The ROI corresponding to the left ventricle is a subset of the heart ROI, identified according to anatomical rules.

In the case the first (or distal) ROI comprises is located in the region of the descending aorta, since the descending aorta is the first location of the arterial tree to receive a pressure pulse passing the center of the EIT image in a vertical and thus well circumscribed location, the descending aorta, or aortic, ROI can be identified as those pixels being situated behind the lungs in the dorsal thorax close to the spine that depict the earliest arrival of the impedance pulse (small PAT values at the time-based image).

In the case the first (or distal) ROI is located in the region of the major branch of the pulmonary artery, since pulse wave velocities (PWV) in the pulmonary circulation are smaller than PWV in the systemic circulation, the major branch of the pulmonary artery, or lung, ROI can be identified as those pixels depicting the latest arrival of impedance pulses (large PAT values within the time-based image).

FIGS. 5(a) to (e) show an example of automatic and unsupervised detection of ROIs by means of time-based EIT imaging. EIT images were obtained from an anesthetized pig. More particularly, FIG. 5(a) represents the time-based image 12 generated by using one of the method discussed above, wherein each pixel of the time-based image is assigned the arrival time (PAT) of its associated impedance pulse. In FIG. 5(b), only those pixels of the time-based image of FIG. 5(a) for which the estimated PAT was reliable enough are selected. FIG. 5(c) shows the heart ROI 3 being identified as the pixels in front of the lungs 4, 5 and depicting the earliest PAT of impedance pulses. FIG. 5(d) shows the aorta ROI 7 being identified as the pixels behind the lungs 4, 5 and depicting the earliest PAT of impedance pulses. FIG. 5(e) shows the right and left lung ROI 4, 5 being identified and depicting the earliest PAT of impedance pulses.

Figure 6:
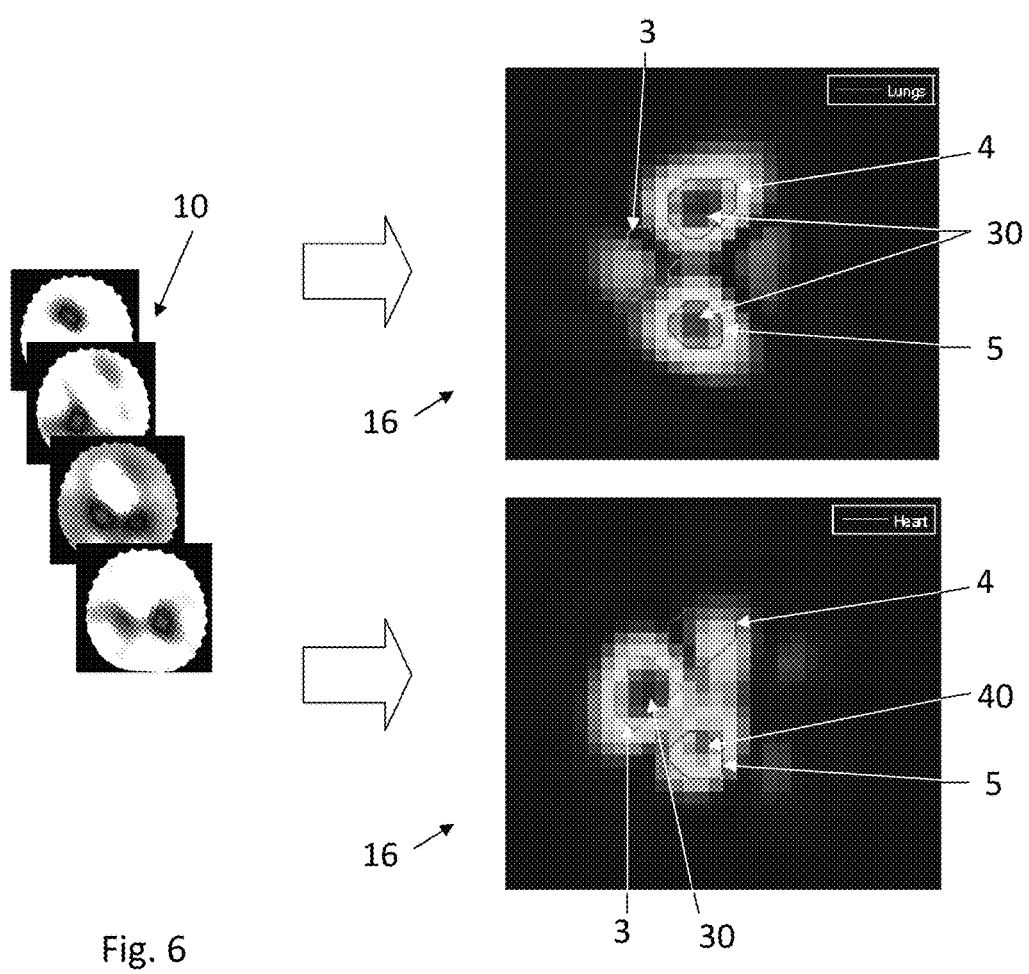
FIG. 6 shows detection of heart and lungs ROI, according to an embodiment.

In an embodiment, energy-based images 16 (see FIGS. 6(a) and (b)) are used for the automatic detection of the proximal ROI and/or the distal ROI. In particular, the spatial distribution of energy for the sequence of EIT images at the respiratory and cardiac frequency bands provides additional information about the location of the heart ROI 3 and lung ROI 4, 5. This is illustrated in FIG. 6. More particularly, FIGS. 6(a) and (b) shows detection of heart 3 and lungs 4, 5 ROI by analyzing the distribution of energy of impedance pulses at different frequency bands. Bright pixels 30 visible by the dark areas indicated by the numeral 30 in FIGS. 6(a) and (b) depict high energy values at the frequency band. EIT images obtained from an anesthetized pig. FIG. 6(a) depicts distribution of energy at the respiratory frequency band, and FIG. 6(b) depicts distribution of energy at the cardiac frequency band.

In other words, the proximal ROI and/or the distal ROI can be determined using one or any combination of the methods comprising: manual or automated analysis of a the EIT image; using spatial distribution of energy for the sequence of EIT images at the respiratory and/or cardiac frequency bands; analyzing the sequence of EIT images to extract arrival time values; and analyzing of images measured from an imaging technique other than the EIT imaging device. The imaging method other than EIT can be a computer tomogram method, or an x-ray imaging method. Alternatively, the imaging method can comprise manual or automatic analysis of a computer tomogram, an x-ray image, or another imaging method.

In another embodiment not represented, only the ROI depicting the distal PAT is identified in the sequence of EIT images, and an external measurement means provides the proximal PAT value. In other words, words, the method further comprises providing a pulsatile measurement device, and estimating the second, or proximal, PAT value by using the pulsatile measurement device. The PAT measurement device, or pulsatile measurement device, can comprise an ECG and the proximal PAT is measured using the the R-Wave of the ECG. Alternatively, the PAT measurement device can comprise an impedance-plethysmographic (IPG) device or a phonocardiographic device; the proximal PAT being measured by using IPG signal of the IPG device, or by using phonocardiographic signal of the phonocardiographic device. Alternatively, the characteristic transient local change in the blood's conductivity as it passes turbulently through the aortic valve can be used to obtain the proximal PAT value.

In another embodiment, the method further comprises calculating a Pulse Wave Velocity value (PWV) by additionally measuring the arterial path length (APL) through which the pressure pulse has travelled. In particular, the PWV values is computed as PWV=APL/PTT. In other words, the method further comprises: measuring an arterial path length (APL) value; and determining a pulse wave velocity (PWV) value as the APL value divided by the PTT value.

Preferred means to assess APL are magnetic resonance imaging, computer tomogram, or morphological measurements performed at the patients (subject). In other words, measuring an APL value comprises using one or a combination of the methods comprising: manual or automatic analysis of images measured from an imaging method other than EIT, and performing at least one morphological measurement of the subject. Said imaging method other than EIT comprises a computer tomogram method, or an x-ray imaging method. While magnetic resonance imaging and computed tomogram provide very accurate measurements of APL, morphological measurements such as body size provide only approximate indirect APL values. A model of the arterial tree including additional anatomical and morphological information might improve the estimation of APL values.

An advantage of the method disclosed herein is that since the calculated PWV value is related to very central and elastic segment of the arterial tree, it provides a clear answer to the guidelines of the European Society of Hypertension, which recommend that measurements of PWV should be performed in elastic arteries if cardiovascular risk is to be assessed or if hypertension is to be diagnosed and managed. Another advantage of the proposed novel method is that measurement of PWV within elastic arteries is performed in a continuous, non-invasive and unsupervised way. The state of the art does not describe any method to measure PWV of elastic arteries in such a continuous, non-invasive and unsupervised way.

Figure 7:
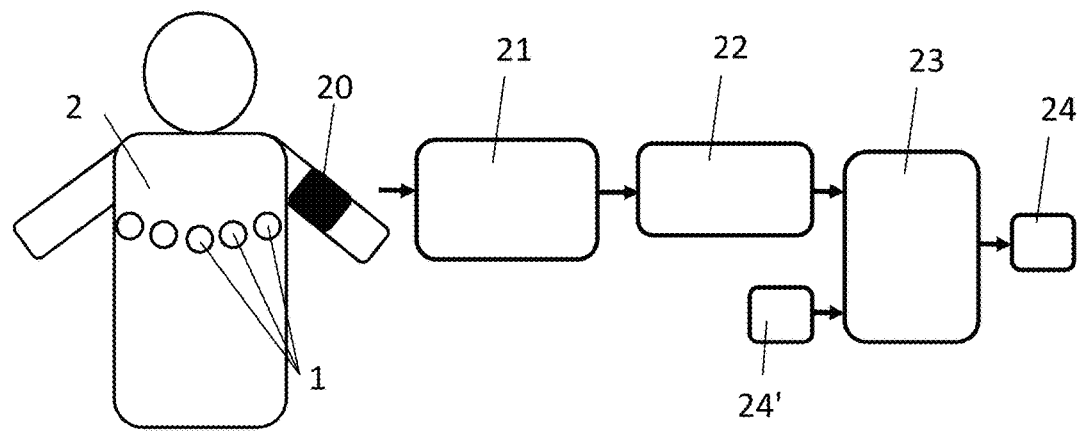
FIG. 7 illustrates a measurement setup for the measurement of blood pressure (BP), according to an embodiment.

The present disclosure also pertains to the use of either the calculated PTT or PWV values to provide continuous, non-invasive and non-obtrusive blood pressure (BP) values. FIG. 7 illustrates an example of a measurement setup and analyzing method allowing the continuous non-invasive and non-obtrusive measurement of BP from the analysis of sequences of time-based EIT images 10, according to an embodiment. The BP measurement setup, or apparatus for the measurement of BP values of the subject comprises the EIT imaging device comprising electrodes 1 disposed around the chest 2 of the subject for measuring the sequence of temporally discrete EIT images 10 of the subject. The BP measurement setup further comprises a processing unit 21, 22 for performing the step of estimating the PAT value, and generating the time-based PAT image. In FIG. 7, although the processing unit is represented by the boxes 21 and 22, it could as well have been represented by a single box. The processing unit 21, 22 is further arranged for calculating the ROI and a first PTT value, a second PTT value and further PPT values using the method disclosed herein. The processing unit 21, 22 is further arranged for converting the first and second PTT value into a first BP and a second BP value, respectively.

The processing unit 21, 22 is further arranged for calculating further BP values by using the calibration factor for calibrating said further PPT values. The BP measurement setup can further comprise a calibration module 23 for determining the calibration factor, and an output module 24 for outputting BP values. The BP measurement setup can further comprise a brachial cuff 20 or an arterial line (not shown) for measuring the reference BP values.

In FIG. 7, the EIT imaging device provides continuous estimates of aortic PWV and BP, the oscillometric cuff 20 intermittently inflates in order to provide new calibration values using the calibration module 23. Signals provided by the brachial or oscillometric cuff 20 are inputted into the calibration module 23 using a input device 24'. The frequency of the intermittent calibration might vary along the day, and according to reliability indexes as provided by the EIT measurement device.

In an embodiment, a method for estimating blood pressure (BP) values comprises:
calculating at least another PTT value and further PPT values using the method for determining PTT value disclosed herein;
determining a calibration factor for converting the PTT value and the at least another PTT value into a first BP and a second BP value, respectively; and
determining further BP values by using the calibration factor for calibrating said further PPT values.

The calibration factor can be determined by measuring reference BP values. The reference BP values can be measured using the brachial cuff 21, 24' or an arterial line (not shown), or any reference BP measuring device. In an embodiment, the calibration factor can be a calibration function.

An advantage of the method for estimating BP values disclosed herein compared to the state of the art, is that the herein provided PWV values are related to very central and elastic segments of the arterial tree. Therefore, since the stiffness of elastic arteries is not modified by vasomotion (as is the case for the stiffness of muscular arteries), the method disclosed will be less affected by changes in the sympathetic and/or parasympathetic tonus continuously occurring during daily life, and will thus reduce the number of calibration periods required. Another advantage of the method disclosed compared to the state of the art, is that since the herein provided PWV values are related to very central and elastic segments of the arterial tree, the influence of orthostatic pressure changes will be minimized, reducing thus the effects that changes in body position have on the calibration strategy. Accordingly, the calculated BP values by means of the method disclosed will be in very close agreement with central BP measurements.

In another embodiment, a PWV value for a segment of the pulmonary arterial tree is calculated using the method disclosed herein. A pulmonary BP value is calculated from the pulmonary PTT or PWV values. While calibration by means of a reference pressure is more challenging for the pulmonary than for the systemic circulation, a method providing non-invasive, continuous and unsupervised monitoring of pulmonary BP variations is proposed. Such a method provides useful information about changes in pulmonary arterial pressure which result from therapeutic measures such as the application of oxygen (O2), nitric oxide (NO) (both leading to a significant vasodilatation and a concomitant fall in pulmonary arterial pressure) as well as inhaled, oral or intravenous medications.

EXAMPLES

Figure 8:
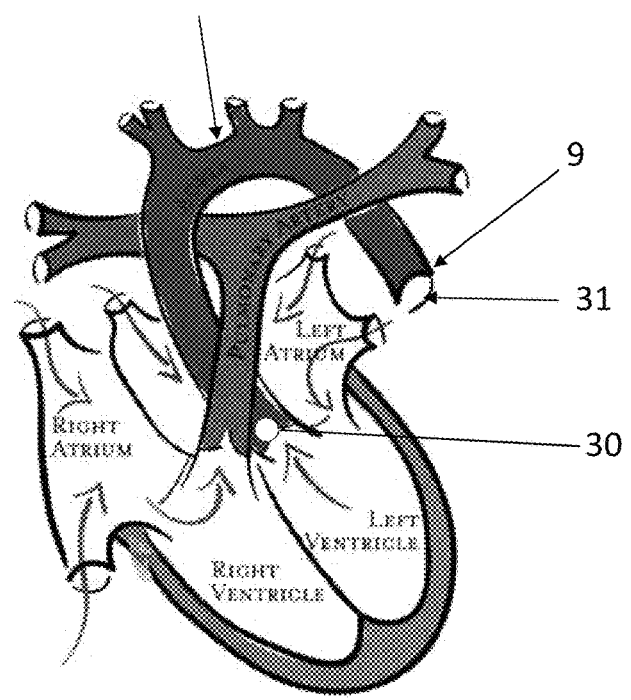
FIG. 8 shows the placement of arterial lines, according to an embodiment.

In the following, an example of non-invasive continuous PTT measurement by means of the herein described method is proposed. The experiment consisted of the monitoring of an anesthetized pig by means of two arterial lines, a first arterial line 30 placed at the aortic arch, close to the aortic valve, and a second arterial line 31 placed at the descending aorta 72, at the level of the EIT electrode plane (see FIG. 8). The placement of the arterial lines 30, 31 can be verified by radiographic means. FIG. 8 shows the placement of the arterial lines: first arterial line 30 is placed distally from the aortic valve 73, and second arterial line 31 is placed at the descending aorta 72, at the EIT field of view.

A sequence of EIT images, recorded at a rate of 50 images per second, is obtained. During the experiment, noradrenalin and nitroglycerine were injected intravenously to induce hypertensive and hypotensive periods, respectively. The processing of the EIT sequence of images was performed by:
initially, generating time-based images for each experimental condition and according to the method described in US provisional patent application Ser. No. 61/344,399. Each time-based image was generated by:
initially detecting the left and/or right-ventricular ROI (energy-based images at the cardiac frequency band were used to support this ROI);

for each pixel within the EIT sequence of images, calculating a 60 seconds ensemble-averaged impedance pulse, using as averaging trigger the onset of left ventricle contraction as determined by the analysis of the impedance pulse at the left- and/or right ventricular ROI;

for each ensemble-averaged impedance pulse, calculating a PAT value according to the TANH parametric modeling described in Reference 8; and by assigning to each pixel in the EIT sequence its calculated PAT value.

Figure 9:
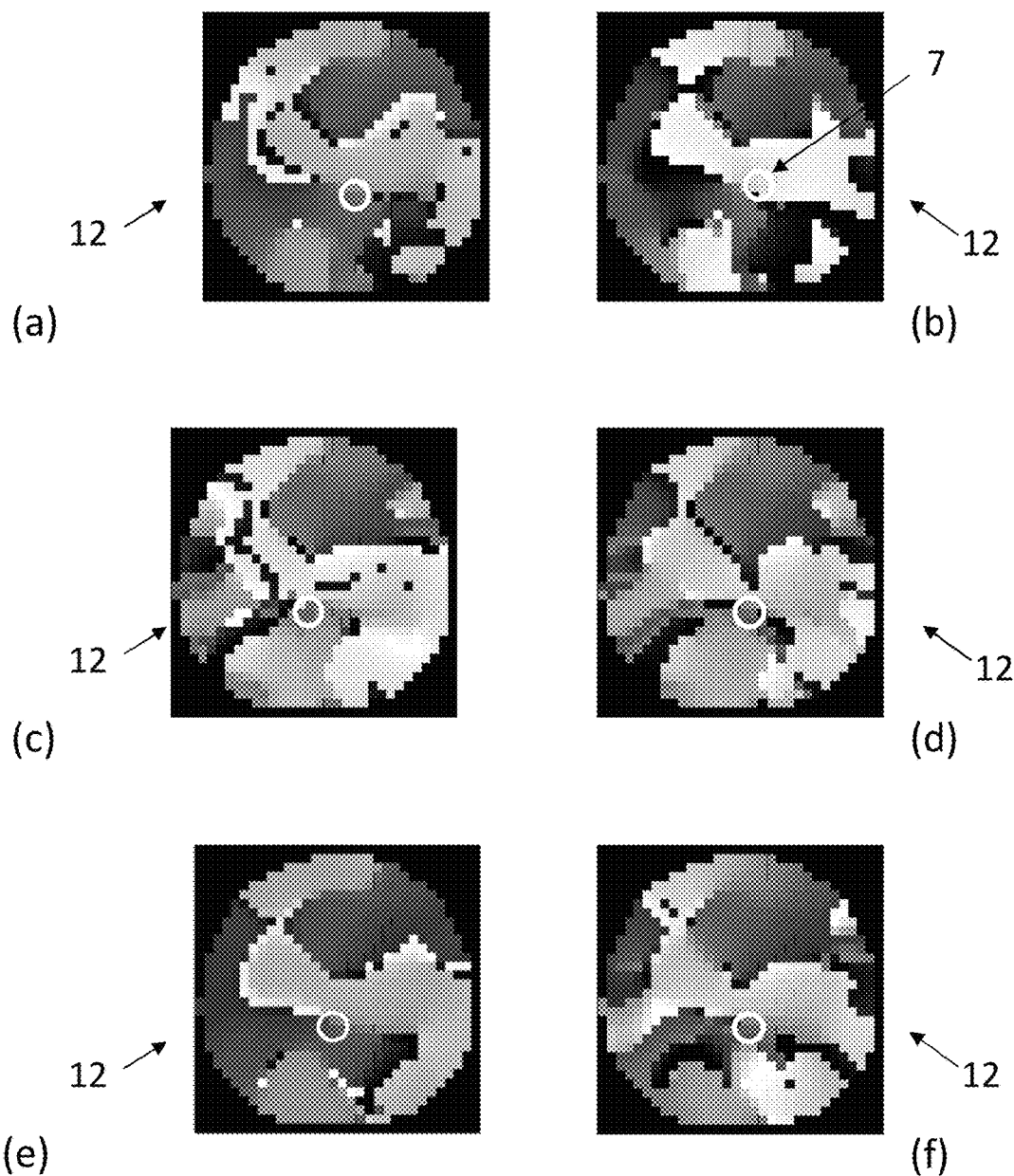
FIGS. 9(a) to (f) illustrate the determination of the aorta ROI within time-based PTT images for different mean arterial pressure conditions, according to an embodiment.

Then, an aortic ROI is identified for each time-based image as those pixels situated behind the lungs and depicting the lowest PAT values in the time-based image. FIG. 9 illustrates the detection of the aortic region 7 at the different time-based images.

Finally, for each experiment, a $PTT_{EIT}$ value is provided as the average of time values at the aortic ROI 7 within the associated time-based image 12. Since the construction of the time-based images 12 used left- and/or right ventricular contraction as ensemble-averaging trigger, the obtained time values already correspond to the transit time from the ventricle(s) to the descending aorta 7.

FIGS. 9(a) to (c) illustrate the determination of the aorta ROI within time-based PTT images 12 for different mean arterial pressure conditions. In the FIGS. 9(a) to (f), the aorta ROI 7 is encircled in white. Each time-based image is computed by estimating the arrival times of 32×32 ensemble-averaged impedance pulses calculated from 60 seconds of EIT images. The onset of left- and/or right ventricular contraction is used as trigger for the ensemble averaging. For the sake of completeness, in the depicted figures the PAT values estimated for all the pixels have been displayed, including those non-reliable PAT estimations. Nevertheless, the detection of the aorta is performed only on those pixels being marked as reliable, as described in the invention and as illustrated in FIG. 5.

The processing of the arterial lines data is performed as follows:

an ensemble-averaged pressure pulse for each arterial line is calculated from 60 seconds of recorded data;

the pulse arrival time of each ensemble-average pressure pulse is calculated via a parametric modeling of the pressure pulse waveform, as described in Reference 8; and a reference PTT value from the arterial line data is obtained for each experimental condition by calculating $PPT_{ref}=PAT_{descending\ aorta}-PAT_{aortic\ valve}$.

In another embodiment not represented, identifying the aortic ROI can be performed by generating an amplitude-based image with the amplitude parameter of the TANH model described in Reference 9. A three-component Gaussian mixture model is then used to characterize the spatial amplitude distribution, thus allowing the localization of the cardiac and pulmonary ROI. The positions of the cardiac and pulmonary ROI are then exploited for defining an aortic search region. In particular, the aortic ROI is identified in the said search region as those pixels with maximal amplitude among those depicting the lowest PAT values. Alternatively, the localization of cardiac and pulmonary ROI can be performed by processing other parameters of the TANH model, or by fitting other parametric models.

Figure 10:
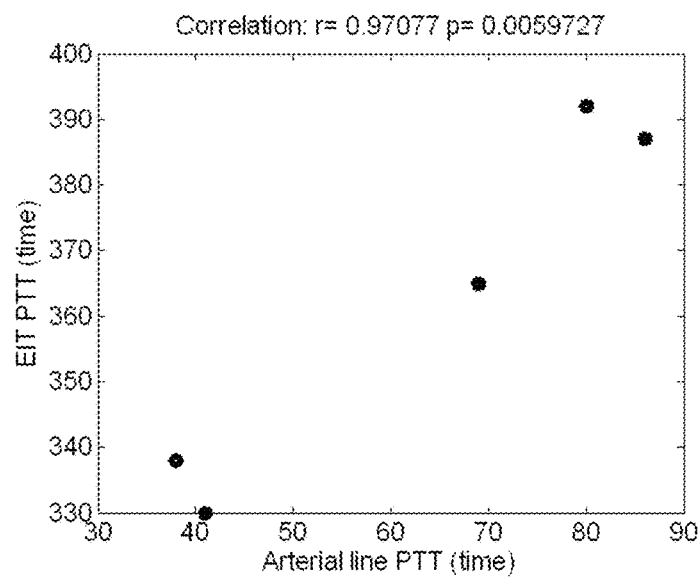
FIG. 10 illustrates the relationship between the calculated $PTT_{EIT}$ and measured pulse transit time (PTT) values for a placement of the arterial lines, according to an embodiment.

In FIG. 10, PTT values from the aortic valve 73 to the descending aorta 72 as simultaneously measured by two arterial line catheters 30, 31, and the herein proposed non-invasive method based on the analysis of sequences of EIT images. Each point depicts a PTT value computed for a segment of 60 seconds of data. High PTT values correspond to normotensive conditions, and low PTT values correspond to hypertensive conditions (the higher the BP, the faster the transit of the pressure pulses, and thus, the smaller the associated PTT values). Differences in absolute times depicted in the figure, are due to the different proximal measurement sites associated with the two different approaches (left ventricle versus aortic valve) and due to the different timing strategies used for two different approaches. In FIG. 10, PTT values of pressure pulses travelling from the aortic valve to the descending aorta are provided, as calculated from both, the arterial line pressure data (invasive), and the sequence of EIT images (non-invasive). Each point in the figure corresponds to 60 seconds at one experimental condition. Only hypotensive and normotensive experimental conditions are displayed since arterial line data during hypertensive measurements were corrupted. High correlation scores for these two measurements are observed (correlation score of 0.97, p<0.01).

Figure 11:
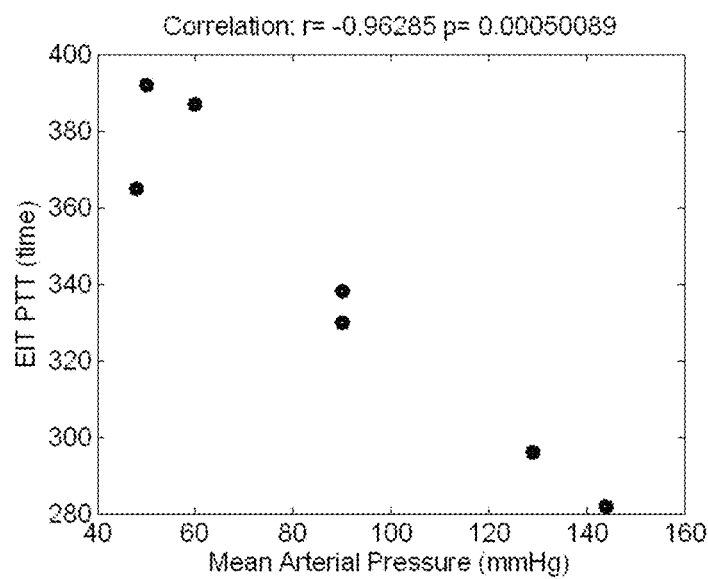
FIG. 11 illustrates the relationship between the calculated $PTT_{EIT}$ and the Mean Arterial Pressure BP, according to an embodiment.

In the following, an example of the use of the herein described method for the continuous, non-invasive and non-obtrusive measurement of blood pressure is provided. For the same experimental conditions already described above, FIG. 11 illustrates the relationship between the calculated $PTT_{EIT}$ and the Mean Arterial Pressure (Blood Pressure, BP) as measured by an aortic pressure sensor (not represented). A high negative correlation index is obtained when comparing these measurements for the normotensive, hypertensive and hypotensive conditions, indicating that $PTT_{EIT}$ is an excellent surrogate of aortic Pulse Wave Velocity: increasing BP induces higher aortic PWV and thus reduced aortic PTT. In FIG. 11, PTT values from the aortic valve to the descending aorta as estimated by the non-invasive method of this invention, compared to simultaneous BP measurements performed by an arterial line. Each point depicts 60 seconds of data for the same anesthetized pig. Note that, as expected, higher BP values are related to smaller estimated PTT values.

Figure 12:
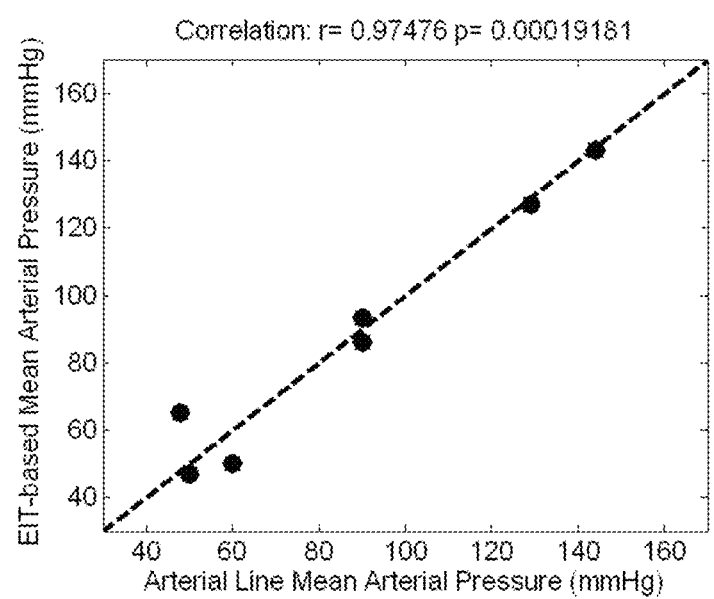
FIG. 12 shows Mean BP measured by an aortic line catheter and by the EIT-based method, according to an embodiment.

In FIG. 12, Mean Blood Pressure is measured by an aortic line catheter and by the non-invasive EIT-based method. Each point depicts 60 seconds of data for the same anesthetized pig. FIG. 12 demonstrates that after a calibration step, $PTT_{EIT}$ measurements can be used to obtain reliable BP estimates in a non-invasive, non-obtrusive and automatic way. In the example, the calibration step consists of estimating a regression line between at least two $PTT_{EIT}$ measurements and their associated simultaneously recorded BP measurements. The regression line is further used to transform each incoming $PTT_{EIT}$ measurements into a BP value.

REFERENCE NUMBERS 1 electrodes
2 chest
3 heart
4 right lung
5 left lung
6 back bone
7 aorta
10 electrical impedance tomography images
12 time-based image, PAT-based image
13 characteristic point
14 pressure pulse waveform
16 energy-based image
20 brachial cuff, oscillometric cuff
21 processing unit
22 processing unit
23 calibration module
24 output module
24' input device 30 first arterial line
31 second arterial line
50 areas with local filling of blood
60 areas with emptying of blood

The invention claimed is:

1. A method for non-invasively monitoring a pulse transit time (PTT) value of a subject, comprising:
    providing an electrical impedance tomography (EIT) imaging device adapted to record an EIT image of the subject, the EIT image comprising an impedance signal distribution;
    during a predetermined measuring time period, measuring a sequence of temporally discrete EIT images of the subject using the EIT imaging device, each EIT image comprising a plurality of pixels, each pixel representing an impedance value; and
    processing the sequence of EIT images to identify at least one region of interest (ROI) comprising a subset of said plurality of EIT pixels;
    estimating at least one of a first arterial pressure pulse arrival time (PAT) value and a second PAT value from a variation of impedance values in said sequence of EIT images from said at least one ROI during the predetermined measuring time period;
    estimating the other of said first PAT value and said second PAT value;
    calculating a PTT value from a difference between the first PAT value and the second PAT value; and
    outputting the PTT value.

2. The method according to claim 1, wherein said determining at least one ROI comprises using one or a combination of the methods comprising:
    manual or automated analysis of the sequence of EIT images, or using spatial distribution of energy for the sequence of EIT images at respiratory and/or cardiac frequency bands.

3. The method according to claim 2, wherein said determining at least one ROI further comprises a computer tomogram method or an x-ray imaging method.

4. The method according to claim 1, wherein said at least one ROI comprises a first ROI at a first location of the arterial tree or the heart of the subject, and a second ROI at a second location of the arterial tree or the heart of the subject.

5. The method according to claim 4, wherein the first location is within a part of the descending aorta and the second location is within a part of the left ventricle.

6. The method according to claim 5,
    wherein a time-based image is generated by computing a PAT value for each pixel in the sequence of EIT images, and
    wherein a ROI corresponding to the heart is identified as the ROI whose pixels depict the lowest PAT values in front of the lungs in the time-based EIT image and a ROI corresponding to the left ventricle comprises a subset of the ROI corresponding to the heart, identified according to anatomical rules.

7. The method according to claim 5,
    wherein a time-based image is generated by computing a PAT value for each pixel in the sequence of EIT images, and
    wherein a ROI corresponding to the descending aorta is identified as pixels in the dorsal thorax behind the lungs depicting the lowest PAT values.

8. The method according to claim 4, wherein the first location is within a part of the major branch of the pulmonary artery and the second location is within a part of the right ventricle.

9. The method according to claim 8,
    wherein a time-based image is generated by computing a PAT value for each pixel in the sequence of EIT images, and
    wherein the right ventricle is identified as the ROI whose pixels depict the lowest PAT values in the time-based EIT image, and the pulmonary artery is identified as the ROI within the central lung region whose pixels depict the PAT values higher than those of the aorta but lower than those depicting the peripheral lung tissue.

10. The method according to claim 1, wherein estimating the second PAT value is performed by using a pulsatile measurement device.

11. The method according to claim 10, wherein the pulsatile measurement comprises an ECG device and the second PAT value is estimated by using the R-Wave measured by the ECG device.

12. The method according to claim 11, wherein the pulsatile measurement device comprises an impedance-cardiographic device, and the second PAT value is estimated by processing impedance-cardiographic signals of the impedance-cardiographic device.

13. The method according to claim 1, further comprising:
    measuring an arterial path length (APL) value; and
    determining a pulse wave velocity (PWV) value as the APL value divided by the PTT value.

14. The method according to claim 13, wherein said measuring an APL value comprises using one or a combination of the methods comprising:
    manual or automatic analysis of images measured from a computer tomogram method or an x-ray imaging method, and
    performing at least one morphological measurement of the subject.

15. The method according to claim 11, wherein the pulsatile measurement device comprises a phonocardiographic device and the second PAT value is estimated by processing phonocardiographic signals of the phonocardiographic device.

16. A non-transitory computer readable medium having computer program product and executable code stored therein that, when executed, causes a computer system to perform the method of claim 1.

* * * * *

UNITED STATES PATENT AND TRADEMARK OFFICE
CERTIFICATE OF CORRECTION

PATENT NO. : 9,999,357 B2
APPLICATION NO. : 13/739025
DATED : June 19, 2018
INVENTOR(S) : Josep Sola i Caros et al.

Page 1 of 1

It is certified that error appears in the above-identified patent and that said Letters Patent is hereby corrected as shown below:

On the Title Page

Please correct the Applicant under item (71), as-follows:
(71) CSEM CENTRE SUISSE D'ELECTRONIQUE ET DE MICROTECHNIQUE
SA - RECHERCHE ET DÉVELOPPEMENT, Neuchatel (CH)

Please correct the third inventor's name and the add the fifth inventor's name under item (72) as-follows:
(72) Inventors:
Josep Sola i Caros, Neuchatel (CH);
Josef X. Brunner, Chur (CH);
Damien Ferrario, Vevey (CH);
Andrew Adler, Ottawa (CA);
Martin Proenca, Marly (CH)

Signed and Sealed this
Second Day of October, 2018

Andrei Iancu
*Director of the United States Patent and Trademark Office*